US008858921B2

(12) United States Patent
Schmid et al.

(10) Patent No.: US 8,858,921 B2
(45) Date of Patent: Oct. 14, 2014

(54) COMPOSITION CONTAINING A WATER-MISCIBLE LIQUID AND A WATER-SOLUBLE PARTICLE, METHOD OF PRODUCTION AND USE THEREOF (75) Inventors: Brenda Schmid, Markt Schwaben (DE); Ingo R. Haeberlein, Weilheim (DE); Bernd Anich, Andechs (DE)

(73) Assignee: 3M Innovative Properties Company, St. Paul, MN (US)

( * ) Notice: Subject to any disclaimer, the term of this patent is extended or adjusted under 35 U.S.C. 154(b) by 373 days.

(21) Appl. No.: 12/921,840

(22) PCT Filed: Mar. 11, 2009

(86) PCT No.: PCT/US2009/036734
§ 371 (c)(1),
(2), (4) Date: Sep. 10, 2010

(87) PCT Pub. No.: WO2009/114581
PCT Pub. Date: Sep. 17, 2009

(65) Prior Publication Data
US 2011/0008270 A1    Jan. 13, 2011

(30) Foreign Application Priority Data
Mar. 13, 2008 (EP) .................................. 08152687

(51) Int. Cl.
*A61K 8/21* (2006.01)
*A61K 8/34* (2006.01)
*A61K 8/60* (2006.01)
*A61K 8/44* (2006.01)
*A61Q 11/00* (2006.01)
*A61K 8/02* (2006.01)
*B82Y 5/00* (2011.01)

(52) U.S. Cl.
CPC ........... *A61Q 11/00* (2013.01); *A61K 2800/412* (2013.01); *A61K 2800/31* (2013.01); *A61K 8/345* (2013.01); *A61K 8/60* (2013.01); *A61K 2800/413* (2013.01); *A61K 8/44* (2013.01); *A61K 2800/652* (2013.01); *A61K 8/0241* (2013.01); *B82Y 5/00* (2013.01)
USPC .......................................................... 424/52

(58) Field of Classification Search
None
See application file for complete search history.

(56) References Cited

U.S. PATENT DOCUMENTS

| 1,572,164 | A | 2/1926 | Shepherd |
| 3,151,027 | A | 9/1964 | Cooley |
| 3,378,445 | A | 4/1968 | Muhler |
| 4,143,126 | A | 3/1979 | Gaffar |
| 4,165,366 | A | 8/1979 | Mellberg |
| 4,165,368 | A | 8/1979 | Gaffar |
| 5,004,596 | A | 4/1991 | Cocherell |
| 5,266,304 | A | 11/1993 | Baffelli |
| 5,630,339 | A | 5/1997 | Tuday |
| 5,804,165 | A * | 9/1998 | Arnold .............................. 424/44 |
| 5,996,864 | A | 12/1999 | Birglechner |
| 6,146,140 | A | 11/2000 | Bailey |
| 6,280,707 | B1 | 8/2001 | Peterson |
| 6,331,291 | B1 * | 12/2001 | Glace et al. ..................... 424/49 |
| 2002/0098156 | A1 | 7/2002 | Milliron |
| 2003/0224702 | A1 | 12/2003 | Roulston |
| 2004/0042976 | A1 | 3/2004 | Silber |
| 2006/0246027 | A1 | 11/2006 | Tanner |
| 2007/0116831 | A1 * | 5/2007 | Prakash et al. ................ 426/548 |

FOREIGN PATENT DOCUMENTS

| DE | 10 2004 020622 | 12/2005 |
| EP | 0528756 | 2/1993 |
| WO | WO 97/02802 | 1/1997 |
| WO | WO 99/30677 | 6/1999 |
| WO | WO 02/02060 | 1/2002 |
| WO | WO 02/39950 | 5/2002 |
| WO | WO 02/45676 | 6/2002 |
| WO | WO 03/091351 | 11/2003 |
| WO | WO 2004/084851 | 10/2004 |

OTHER PUBLICATIONS

Journal of Dental Research, A Laboratory Method for Assessment of Dentrifrice Abrasivity; Hefferren; 55/4 (Jul./Aug. 1976), pp. 563-573.
ANSI/ADA Spec. No. 62-2005; American National Standard/American Dental Association Specification No. 62 for Dental Abrasive Pastes; 12 pgs, Feb. 17, 2005.
European Search Report/Opinion (EP 08152687.3-64040EP002) Nov. 11, 2008; 2 pgs.
International Search Report PCT/US2009/036734; Jun. 17, 2010, 3 pgs.
Claude Laguerie et al, "Some physicochemical data on monohydrate citric acid solutions in water: solubility, density, viscosity, diffusivity, pH of standard solution, and refractive index", Journal of Chemical & Engineering Data, vol. 21, No. 1, Jan. 1, 1976, pp. 85-87.

* cited by examiner

*Primary Examiner* — Snigdha Maewall
(74) *Attorney, Agent, or Firm* — Nicole J. Einerson

(57) ABSTRACT

The invention relates to a water-soluble composition comprising a water miscible liquid and water-soluble particles, the water-soluble composition being essentially free of water. The composition can be used e.g. as dental composition, cleaning agent, polishing agent, tongue surface cleaning agent or peeling agent.

14 Claims, 3 Drawing Sheets

COMPOSITION CONTAINING A WATER-MISCIBLE LIQUID AND A WATER-SOLUBLE PARTICLE, METHOD OF PRODUCTION AND USE THEREOF

CROSS-REFERENCE TO RELATED APPLICATIONS

This is a national stage filing under 35 U.S.C. 371 of PCT/US2009/036734, filed Mar. 11, 2009, which claims priority to European Patent Application No. 08152687.3, filed Mar. 13, 2008, the disclosure of which is incorporated by reference in its/their entirety herein.

FIELD OF THE INVENTION

The invention relates to a composition comprising a water-miscible liquid and water-soluble particles. The water-soluble particles are essentially non-soluble in the water-miscible liquid. Possible uses of the composition include the use as a dental composition, cleaning agent, polishing agent or peeling agent.

BACKGROUND ART

The use of cleaning and polishing agents as oral care agents is commonly known.

US 2004/0042976 (Silber) deals with an abrasive component as a cleaning agent in a semi-solid or liquid cleaning product having an abrasive action containing platelet-shaped particles such as glass flakes.

U.S. Pat. No. 5,266,304 (Baffelli) describes a water-free prophylactic paste containing at least 40 wt.-% of perlite.

U.S. Pat. No. 6,280,707 B1 (Peterson) refers to an oral prophylaxis paste containing a pre-selected grade and amount of abrasive material such as pumice clay or diatomaceous earth, moistened with water.

WO 2004/084851 A2 (Rochat) discloses a dental treatment composition comprising a particulate erasing agent having particles which are dimensions to roll along a surface. The composition contains at least 3% water and the particulate erasing agent comprises a precipitate or agglomerate of an insoluble alkali metal carbonate.

US 2002/0098156 A1 (Milliron) deal with a prophylaxis paste containing Roxite particles (zirconium-oxide based polishing powder).

U.S. Pat. No. 5,004,596 describes an anhydrous toothpaste or dental cream composition comprising inter alia 6 to 90% by total weight of one or more hydrogenated vegetable oils, 0.02 to 25% by total weight of one or more flavouring oils or extracts, 0.1 to 60% by total weight of glycerine and 10 to 90% by total weight of one or more inorganic salts selected from sodium bicarbonate, magnesium sulphate and sodium chloride.

None of the above outlined procedure is fully satisfying to the practitioner.

Thus, there is still room for improvement especially with regard to the requirements to be fulfilled with respect to modern dental materials and cleaning or polishing agents or compositions.

Ideally, a composition is desired, that is low abrasive and can be used for cleaning and/or polishing surfaces including the surface of hard dental tissue (e.g. natural teeth), the surface of dental filling materials, dentures or orthodontic appliances.

DESCRIPTION OF THE INVENTION

In one aspect the invention features a water-soluble composition comprising a water-miscible liquid and
water-soluble particles,
the water-soluble composition being essentially free of water.

In another aspect the invention features a method of preparing a water-soluble composition comprising the step of combining a water-miscible liquid with water-soluble particles.

A further aspect of the invention is directed to a kit of parts comprising part I and part II, part I comprising a water-miscible liquid and part II comprising a water-soluble particle, part I and part II being separated from each other before use, the part I and part II being essentially free of water.

Yet another aspect of the invention is directed to a method of using the composition or the kit of parts as dental composition, cleaning agent, polishing agent, or peeling agent (e.g. for skin, hard dental tissue, surfaces of dental filling materials, tongue surfaces and/or orthodontic appliances), A further aspect of the invention is directed to a kit of parts comprising part A and part B, part A comprising the water-soluble composition or the kit of parts described in the text of the invention and part B comprising a polishing device.

Yet another aspect of the invention is directed to the use of water-soluble particles for the production of a water-soluble cleaning or polishing composition containing a water-miscible liquid, the water-soluble composition being essentially free of water, wherein the water-soluble particles and the water-miscible liquid are as described in the text of the present invention.

Within the description of the invention, the following terms are defined as follows:

A "composition" is understood to be a mixture of two or more components.

A "tooth structure" is any tooth structure, prepared or ready for preparation by the dentist. It can be a single tooth or two or more teeth. A tooth structure is also referred to as hard dental tissue in contrast to soft dental tissue (e.g. gingival).

A "paste" is a substance that behaves as a solid until a sufficiently large load or stress is applied, at which point it flows like a fluid. Pastes typically consist of a suspension of granular material in a background fluid. The individual grains are jammed together like sand on a beach, forming a disordered, glassy or amorphous structure, and giving pastes their solid-like character. Pastes can be classified by their viscosity or their consistency comparable to dental impression material (cf. ISO 4823).

A "toothpaste" (dentifrice) is a cleaning agent for the daily individual care. It is typically used as a prophylactic measure against caries, gingivitis or periodontitis. In contrast to this, a "prophylaxis paste" is a product which is used by a profession such as a dentist or a dental hygienist to remove adherent deposits such as stain, plaque or tartar which may stick to the surface of a natural tooth, artificial tooth crown or bridge or filling material. A prophylaxis paste is therefore typically used on slowly rotating paste carrier (sometimes also referred to as prophy cups). Most of the commercially available prophylaxis pastes have a different viscosity compared to tooth pastes.

Toothpastes and prophylaxis pastes can be classified e.g. by their relative abrasion of enamel and/or dentin REA values refer to the relative abrasion of enamel, whereas RDA values refer to the relative abrasion of dentin caused by tooth paste. PPEA values refer to the relative abrasion of enamel, whereas PPDA values refer to the relative abrasion of dentin caused by prophylaxis paste. A measuring method is described in the Journal of Dental Research 55/4 (1978), 563 (see also ANSI/ADA Specification No. 62-2005 and German Industry Standard DIN EN ISO 11609).

A "gel" is typically a colloidal system in which a porous matrix of interconnected particles spans the volume of a liquid medium. In general, gels are apparently solid, jelly-like materials. Both by weight and volume, gels are mostly liquid in composition and thus exhibit densities similar to liquids, however, have the structural coherence of a solid. An example of a common gel is edible gelatin. Many gels display thixotropy, that is, they become fluid when agitated, but resolidify when resting.

The term "water-miscible" means that a certain liquid is miscible with water at 23° C. at least to a high extend to provide a homogeneous solution, i.e. without phase separation. More specifically, the water-miscible liquid is defined as miscible with water if at least 10 g or at least 100 g or at least 500 g or at least 750 g or least 1000 g water-miscible liquid is soluble in 1000 g water without phase separation. Ideally, no phase separation occurs at ambient conditions independent from the mixing ratio (e.g. ethanol is miscible with water in all ratios).

The term "water-soluble" means that a substance as such is soluble in water at ambient conditions, comparable to a salt. That is, the substance is able to form individual molecules in water like glucose when dispersed in water at 23° C.

More specifically, according to the invention a substance or composition is defined as water-soluble, if less than about 10 wt.-% or less than about 5 wt.-% or less than about 2 wt.-% or less than about 1 wt-% or less than about 0.1 wt.-% (with respect to the whole composition) of substance remains after the following procedure:
a) 800 mg of substance or composition and 8.0 g demineralised water are placed into a centrifuge test tube of known weight.
b) The test tube is closed and shaken for 5 minutes.
c) The mixture is centrifuged with centrifugal acceleration (ac) of 9870 m/s$^2$ for 20 min.
d) The supernatant liquid is decanted.
e) The precipitate is re-suspended with 6 g demineralised water.
f) The test tube is shaken for 5 min, centrifuged as described above, and the supernatant liquid decanted again.
g) Steps e) and f) are repeated one time.
h) The remaining precipitate is kept for 12 h at 23° C., followed by 12 h drying at 105° C. (+/−3.5° C.).
i) After cooling to room temperature in a desiccator the dry weight of the sample is determined and used for calculating the water soluble fraction.

A substance or composition is defined as water-insoluble, if more than about 90 wt.-% or more than about 50 wt.-% or more than about 25 wt.-% or more than about 10 wt.-% (with respect to the whole composition) of substance remains unsolved after the procedure described above.

A "particle" means a substance being a solid having a shape which can be geometrically determined. Particles can typically be analysed with respect to e.g. grain size.

The mean particle size of a powder can be obtained from the cumulative curve of the grain size distribution and is defined as the arithmetic average of the measured grain sizes of a certain powder mixture. Respective measurements can be done using commercially available granulometers (e.g. CILAS Laser Diffraction Particle Size Analysis Instrument).

"Mohs hardness" means the scale of hardness characterized by the scratch resistance, that is, the ability of a harder material to scratch a softer material.

On the Mohs scale, e.g. a pencil lead has a hardness of 1; a fingernail has hardness 2.5; a copper penny, about 3.5; a knife blade, 5.5; window glass, 5.5; steel file, 6.5; talc ($Mg_3Si_4O_{10}(OH)_2$) has a hardness of 1, gypsum ($CaSO_4*2H_2O$) has a hardness of 2, calcit ($CaCO_3$) has a hardness of 3, fluorite ($CaF_2$) has a hardness of 4, apatit ($Ca_5(PO_4)_3(OH^-,Cl^-,F^-)$) has a hardness of 5; perlit has a hardness of 5.5; pumice has a hardness of 6.

Unless otherwise defined "density" means specific density, i.e. mass per volume. The mass is normally measured with an appropriate scale; the volume may be measured directly (from the geometry of the object) or by the displacement of a liquid. A very common instrument for the direct measurement of the density of a liquid is the hydrometer. A less common device for measuring fluid density is a pycnometer, a similar device for measuring the absolute density of a solid is a gas pycnometer. Unless otherwise specified, the density referred to in the present invention are the values which can be taken from common textbooks like Beilstein database or Römpp Chemie Lexikon and refers to the density obtained by analyzing a compact, non-porous particle.

A "dental compositions and dental articles" is a composition which is to be used in the dental field (including restorative and prosthodontic work) including the orthodontic area. In this respect the composition should be not detrimental to the patient's health and thus free of hazardous and toxic components being able to migrate out of the composition. Commercially available products have to fulfil certain requirements such as those given in DIN EN 21942-2.

A substance is classified as "liquids" if it has a viscosity below about 100 Pa*s or below about 50 Pa*s or below about 5 Pa*s at 25° C.

If not otherwise indicated "molecular mass" always means Mw (weight average molecular mass) and can either be taken from the product specification or can be determined by suitable measurement methods known to the person skilled in the art, such as sedimentation velocity.

The term "essentially free of a substance" is to be understood that a certain substance is typically not present at all or has not been willfully added. However, it might happen that sometimes unavoidable traces of this substance can be detected such as water absorbed or adsorbed on the surface of an additive.

Thus, "essentially free of water" means that the content of water (especially added water) in a composition is less than about 5 wt.-% or less than about 2 wt.-% or less than about 1 wt.-% or less than about 0.1 wt.-% with respect to the whole composition. Small amounts of water incidentally may be present, e.g. as by-product of chemical reactions or as a result of absorption from the environment.

A "kit of parts" means a packaging unit comprising at least two parts. The kit may comprise an outer packaging unit, which in turn may comprise one or more inner packaging units. The kit further may comprise one or more additional compositions, a delivery enhancement device, instructions for use of the device, instructions for complying with suitable application regimes, combinations thereof and the like.

"Ambient conditions" mean the conditions which the inventive composition is usually subjected to during storage and/or handling. Ambient conditions may, for example, be a pressure of about 900 to about 1100 mbar, a temperature of about −10 to about 60° C. and a relative humidity of about 10 to about 100%. In the laboratory ambient conditions are typically adjusted to about 23° C. and about 1013 mbar.

As used herein, "a", "an", "the", "at least one" and "one or more" are used interchangeably. The terms "comprises" or "contains" and variations thereof do not have a limiting meaning where these terms appear in the description and claims. Also herein, the recitations of numerical ranges by endpoints include all numbers subsumed within that range (e.g., 1 to 5 includes 1, 1.5, 2, 2.75, 3, 3.80, 4, 5, etc.).

Unless otherwise indicated, all numbers expressing quantities of ingredients, measurement of properties such as contrast ratio and so forth used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings of the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviations found in their respective testing measurements.

DETAILED DESCRIPTION OF THE INVENTION

If the inventive water-soluble composition is used as a cleaning, polishing or peeling agent, the composition typically shows only little abrasion on the treated surface, especially with regard to the surface of dental tissue (e.g., tooth enamel and dentin), dental filling materials (including dental composite materials (e.g. Filtek™, 3M ESPE Comp.), resin-modified glass ionomer cements (e.g. Ketac™, 3M ESPE Comp.)), orthodontic materials, brackets or appliances (fixed and removable).

Without wishing to be bound to a certain theory, it is believed that the presence of water-soluble components in the water-soluble inventive composition and/or the absence of larger amounts of hard and/or water-insoluble particles contribute to this advantage.

Figure 1:
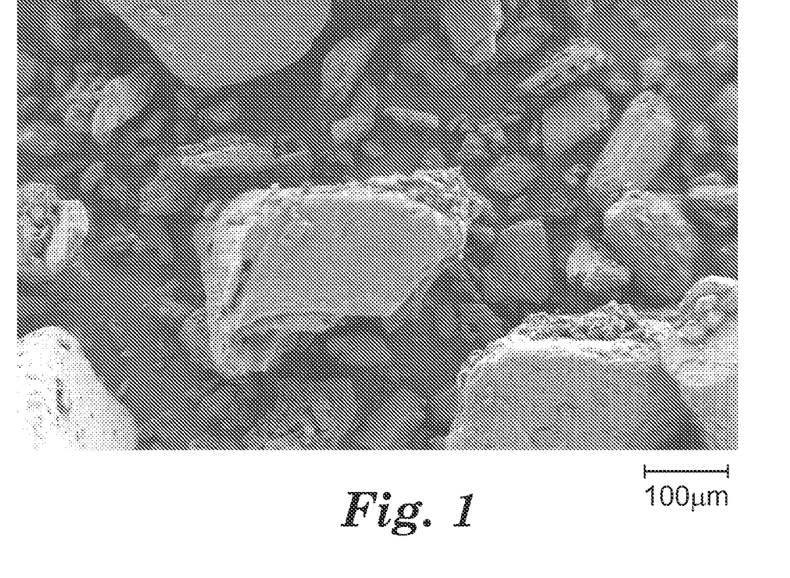
FIGS. 1 and 2 show SEM (scanning electron microscope) pictures of an embodiment of the inventive composition before and after use as a polishing agent.
Figure 2:
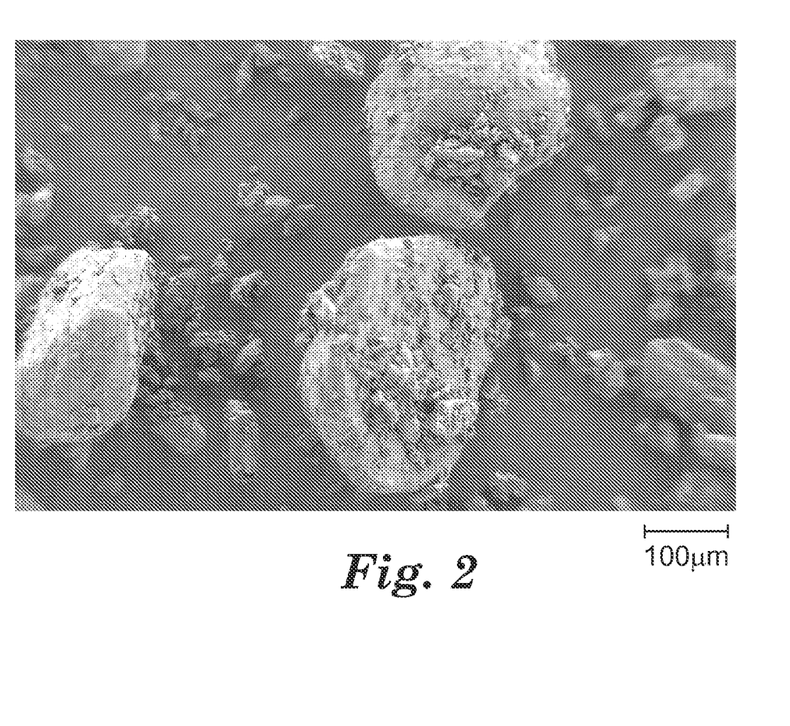

E.g., it has been observed that during the use of the inventive composition e.g. in a tooth cleaning or polishing procedure, the water-soluble particles dissolve in water being present in the saliva of a patient's mouth at least partially over time wherein the particle size decreases and rough or sharp edges of the particles of the water-soluble particle disappear (as shown in FIGS. 1 and 2). It has been found that surfaces treated with the inventive composition typically stay very smooth.

Furthermore, it has been found that surfaces treated with the inventive composition essentially keep their original glossy appearance and do not get a matt appearance.

Despite the feature that the water-soluble particles used in the inventive composition are essentially non-soluble in the water-miscible liquid used, the water-soluble particles are soluble in water being present at the location to be treated, e.g. water contained in saliva.

Another positive side-effect of using water-soluble particles is that particles pushed below the gum line or splattered in the oral cavity of the treated patient, are typically dissolved over time by saliva present in the patients' mouth. Thus, depending on the formulation chosen, the inventive composition is usually tissue-friendly. This feature can be beneficial, if a chemically sensitive patient is to be treated. Thus, there is no need to mechanically remove particles which might have been pushed in the interdental space or under the gumline during a treatment. A simple rinsing of the mouth with water is sufficient to remove or dissolve remaining particles.

Typically, the inventive composition has a gel-like or paste-like consistency. This might help to reduce splattering of the composition, if e.g. a rotating polishing device is used during the polishing or cleaning procedure.

Depending on the components chosen, the inventive composition may have a pleasant taste, even without the presence of flavourants or sweeteners and/or cause a less gritty mouth feeling compared to commercially available prophylaxis pastes.

The inventive composition is essentially free of added water or may contain water in only very small amounts, e.g., less than about 5 wt.-% or less than about 2 wt.-% or less than about 1 wt.-% with respect to the whole composition.

According to one aspect of the invention, the inventive composition can be characterized by at least one of the following features:
Consistency: below about 35 mm or below about 20 mm or below about 10 mm Pa*s at 23° C. (measured according to the procedure described in the experimental section).
pH-value (10 g of the composition dissolved in 30 g water): below about 11 or below about 7 or above about 2.

A pH-value below about 2 is usually not desirable. A low pH-value might cause damage not only to a tooth surface but also to packaging containers. Also the stability of the ingredients of the composition might be negatively influenced. The same typically holds true for a pH-value above about 11.

The inventive composition typically contains less than about 15 wt.-% or less than about 10 wt.-% or less than about 1 wt.-% of water-insoluble particles, especially particles having a Mohs hardness greater than about 3 or about 5, (wt.-% with respect to the whole composition). In a specific embodiment, the inventive composition is essentially free of water-insoluble particles having a Mohs hardness of above about 5.

According to a further embodiment, the inventive composition comprises less than about 10 wt.-% or less than about 8 wt.-% or less than about 5 wt.-% or less than about 2 wt.-% of either or more of the following components: sodium bicarbonate, sodium carbonate, sodium chloride, magnesium sulfate and starch, wt-% with respect to the whole composition.

According to a further embodiment, the inventive composition comprises less than about 5 wt.-% sodium bicarbonate, less than about 5 wt.-% sodium carbonate, less than about 5 wt.-% sodium chloride, less than about 5 wt.-% magnesium sulfate and less than about 5 wt.-% starch, wt-% with respect to the whole composition.

The inventive composition comprises a water-miscible liquid.

The chemical and physical nature of the water-miscible liquid is not particularly limited. Generally speaking, any liquid can be used which fulfils the intended purpose and is water-miscible. Preferably, the water-miscible liquid is biologically degradable and non-toxic to human beings.

According to another embodiment, the water-miscible liquid can be characterized by at least one of the following features:
  Boiling point: below about 300° C. or below about 200° C. or below about 100° C., or above about 50° C.;
  Viscosity: below about 100 Pa*s (23° C.) or below about 50 Pa*s (23° C.) or below about 5 Pa*s (23° C.);
  Molecular mass: below about 100,000 or below about 10,000 or below about 1,000 or below about 500 or below about 100 (g/mol).

The water-miscible liquid is typically present in the inventive composition in an amount of at least about 5 wt.-% or at least about 10 wt.-% or at least about 20 wt.-% with respect to the whole composition.

The water-miscible liquid can be present in an amount of up to about 90 wt.-% or up to about 70 wt.-% or up to about 50 wt.-% with respect to the whole composition.

Typical ranges are from about 5 to about 90 wt.-% or from about 10 to about 70 wt.-% or from about 15 to about 50 wt.-% with respect to the whole composition.

Specific examples of water-miscible liquid, which can be used, include polyols (including glycol, glycerol, polyethylene glycol (e.g. PEG 200, PEG 400, PEG 600), 1,2-propanediol and 1,3-propanediol), glycerole ether (including glycerol-1-buthyl-3-isostearylether), and alcohols (including n- and iso-propanol and ethanol) and mixtures thereof.

The inventive dental composition comprises water-soluble particles.

The chemical and physical nature of the water-soluble particle is not particularly limited. Generally speaking, any component can be used which fulfils the intended purpose and is water-soluble. Typically, the water-soluble particles are non-soluble in the water-miscible liquid.

According to a certain embodiment, the water-soluble particle can be characterized by at least one or more of the following features:
  mean particle size below about 500 μm or below about 300 μm or below about 250 μm,
  density below about 4.5 g/ml or below about 3.0 g/ml or below about 2.0 g/ml,
  molecular mass (Mr) of the substance, the particles are made or comprised of: in the range of about 10,000 to about 40 or of about 1,000 to about 50 or of about 500 to about 60.
  Solubility of the water-soluble particles in the water-miscible liquid: below about 5 wt.-% or below about 10 wt.-% or below about 20 wt.-% or below about 60 wt.-%.

The solubility of the water-soluble particles in the water-miscible liquid can be determined as defined above.

According to a specific embodiment, the mean particle size of the water-soluble particles is in a range of about 20 to about 500 μm or in a range of about 50 to about 250 μm or in a range of about 100 to about 200 μm.

The mean particle size can be measured as described in the examples section below using a commercially available instrument such as CILAS Laser Diffraction Particle Size Analysis Instrument and following the respective instruction of use provided by the manufacturer.

Unless indicated otherwise, density usually means specific density and is typically taken from the respective manufacturer specification or literature available to the skilled person in the art.

The water-soluble particles are typically present in the inventive composition in an amount of at least about 10 wt.-% or at least about 25 wt.-% or at least about 40 wt.-% with respect to the whole composition.

The water-soluble particle can be present in an amount of up to about 95 wt.-% or up to about 75 wt.-% or up to about 50 wt.-% with respect to the whole composition.

Typical ranges include from about 10 to about 95 wt.-% or from about 15 to about 90 wt.-% or from about 25 to about 80 wt.-% with respect to the whole composition.

Examples of water-soluble particles, which can be used, include organic acids and their salts (including alkaline metal salts, alkaline earth metal salts, ammonium salts), amino acids and their salts, sugars, alkaline metal salts and alkaline earth metal salts and mixtures thereof.

That is, besides particles comprising substances selected from organic acids and their salts, amino acids and their salts, sugars, and mixtures thereof, the composition may include further water-soluble particles.

Specific examples of organic acids and their salts include citric acid, ascorbic acid, ketoglutarsäure, pyruvic acid, sodium lactate and mixtures thereof.

Specific examples of amino acids and their salts include glycine, alanine, glutamine, glutamic acid, serine, valine, leucine, iso-leucine, potassium glutamate, sodium glutamine and mixtures thereof.

The term "sugar" refers to any monosaccharide or disaccharide. Specific examples of sugars include xylitol, sorbitol, glucose, fructose, saccharose and mixtures thereof.

In contrast to sugar, cellulose is a polysaccharide consisting of a linear chain of several hundred to over ten thousand β(1→4) linked D-glucose units. Cellulose with in the meaning of the present invention is not a sugar. The same holds true for starch. Starch is a polysaccharide carbohydrate consisting of a large number of glucose monosaccharide units joined together by glycosidic bonds.

Specific examples of alkaline metal salts include sodium chloride, potassium chloride, sodium carbonate, sodium hydrogen carbonate, sodium phosphate, sodium dihydrogen phosphate, sodium hydrogen phosphate, sodium pyrophosphate, sodium sulphate, potassium phosphate, potassium hydrogen phosphate, potassium dihydrogen phosphate, potassium carbonate, potassium hydrogen carbonate and mixtures thereof.

Specific examples of alkaline earth metal salts include calcium chloride, calcium hydrogen carbonate, magnesium chloride, calcium nitrate and mixtures thereof.

Depending on the surrounding environment and the liquids present, some of these substances might behave as a chemical buffer.

The inventive composition can be comprised of the water-soluble particle and the water-miscible liquid only. However, it is also possible that the composition further comprises additives.

The chemical and physical nature of the additives, which can be used, is not particularly limited. Generally speaking, any additive can be used which is not contra productive to the intended purpose. In this respect, the additives taken alone might be characterized as water-soluble or water-insoluble according to the invention. Using water-soluble additives can be preferred.

Additives which can be included in the composition include stabilizer(s), fluoride releasing agent(s), anti-microbial agent(s), colourant(s), buffer(s), surfactant(s), phosphate releasing agent(s) and mixtures thereof.

Most of these additives are water-soluble according to the definition of the invention. In the event that they are not water-soluble, these additives are only present in the composition in a small amount, e.g. in an amount below about 5 wt.-% or below about 2 wt.-% or below about 0.5 wt.-% with respect to the whole composition.

Additive(s), if present at all, are typically present in an amount of up to about 30 wt.-% or up to about 20 wt.-% or up to about 10 wt.-%, with respect to the whole composition.

According to one embodiment, the dental composition comprises additives in an amount of 0 to about 30 wt.-% or 1 to about 20 wt.-% or 5 to about 15 wt.-% with respect to the whole composition.

If the additives are present as solid particles, the mean particle size of the additives might differ from the particle size of the water-soluble particle described in the text of the invention. The particle size of the additives might be larger or smaller. Typically, the mean particle size of the additives is within a range of about 10 µm to about 500 µm or about 50 µm to about 250 µm or about 50 to about 150 µm.

The additives, if present at all, can also be in a liquid state.

The inventive composition might contain one or more stabilizer(s) as an additive. If a stabilizer is present, the storage stability of the dental composition might be improved. That is, the individual components of the composition do not separate over time. A composition according to the invention is defined as storage-stable, if the components do not separate from each other within about 6 months or about 12 months or about 24 months or about 36 months at ambient conditions.

If a stabilizer is present, it is typically, present in a low amount. Amounts, found to be useful, include 0.001 to about 15 wt.-% or about 0.01 to about 5 wt.-% or about 0.1 to about 3 wt.-% with respect to the weight of the whole dental composition.

Examples of stabilizer(s), which can be used, include xanthane (e.g. Xanthane Gum™, Jungbunzlauer Comp.), coplymere of 2,5-furandione with 1,9-decadiene and methoxyethene (e.g. Stabileze™, International Specialty Products (ISP) Comp.) and carboxy vinyl polymers (e.g. Carbopol™, Lubrizol Advanced Materials Comp.).

Stabilizers typically have a mean particle size below about 500 µm_or below about 250 µm_or below about 100 µm.

In another embodiment, the composition can comprise one or more fluoride releasing agents as an additive.

There is no need for a fluoride releasing agent to be present at all. However, if it is present, it is typically present in an amount of at most about 10 wt.-% or of at most about 5 wt.-% or of at most about 2 wt.-% with respect to the amount of the whole composition. Typical ranges include from 0.01 wt.-% to about 10 wt.-% or from 0.1 wt.-% to about 5 wt.-% with respect to the amount of the whole composition.

Examples of fluoride releasing agent, which can be used, include sodium fluoride, potassium fluoride, stannous fluoride, N,N,N'-Tris(2-hydroxyethyl)-N'-octadecyl-1,3-diaminopropan-dihydrofluorid (amine fluoride), sodium monofluorophosphate and mixtures thereof In a further embodiment, the dental composition comprises one or more colourants.

There is no need for a colourant to be present at all. However, if it is present, it is typically present in an amount of at most about 5 wt.-% or of at most about 2.5 wt.-% or of at most about 1 wt.-% with respect to the amount of the whole composition. Typical ranges include from 0.01 wt.-% to about 5 wt.-% or from 0.1 wt.-% to about 2.5 wt.-% with respect to the amount of the whole composition.

The presence of a colourant may allow an easy detection in a patients' mouth (especially compared to oral tissue and/or tooth substance) and control whether after the treatment all residues of the composition have been removed. E.g., a blue, green or violet colour may be suitable. Colouring of the dental composition can be achieved by incorporating colorants or pigments (organic and inorganic) into the composition.

Examples of colourants which can be used include red iron oxide 3395, Bayferrox 920 Z Yellow, Neazopon Blue 807 (copper phthalocyanine-based dye) or Helio Fast Yellow ER and mixtures thereof.

In a further embodiment, the dental composition comprises one or more phosphate releasing agent(s) as an additive.

There is no need for a phosphate releasing agent to be present at all, however, if it is present, it is typically present in an amount of at most about 10 wt.-% or of at most about 5 wt.-% or of at most about 2 wt.-% with respect to the amount of the whole composition. Typical ranges include from 0.01 wt.-% to about 10 wt.-% or from 0.1 wt.-% to about 5 wt.-% with respect to the amount of the whole composition.

Examples of phosphate releasing agent(s) which can be used include calcium pyrophosphate, calcium carbonate, dicalcium phosphate dehydrate, amorphous calcium phosphate, casein phosphopeptide, calcium sodium phosphosilicate, trimetaphopshate, and mixtures thereof.

In another embodiment, the dental composition comprises an anti-microbial agent.

There is no need for an anti-microbial agent to be present at all. However, if it is present, it is typically present in an amount of at most about 2 wt.-% or of at most about 1 wt.-% or of at most about 0.5 wt.-% with respect to the amount of the whole composition. Typical ranges include from 0.01 wt.-% to about 2 wt.-% or from 0.1 wt.-% to about 1 wt.-% with respect to the amount of the whole composition.

The presence of an anti-microbial agent might help reducing health risks for professionals in the dental offices and laboratories as well as for patients.

Useful anti-microbial agents include chlorhexidine or derivatives thereof and aldehydes (glutaraldyde, phtalaldehyde) and chlorhexidine or its derivatives and salts of phenolics or acids. It can also be preferred to use acid adducts of chlorhexidine or its derivatives like e.g., acetates, gluconates, chlorides, nitrates, sulfates or carbonates.

Chlorhexidine and its derivatives (hereinafter referred to as CHX) are commercially available in water-based solutions (e.g. a 20% aqueous solution of CHX digluconate, CAS 18472-51-0) or as a pure compound or as a salt. As additive the pure Chlorohexidine compound (CAS 55-56-1) and CHX salts like CHX diacatate monohydrate (CAS 56-95-1) or CHX dihydrochloride (CAS 3697-42-5) are preferred.

CHX also seems to be especially suited as an additive due in part to its well-known and proven anti-microbial action against Gram positive and Gram negative microorganisms including the oral Streptococci and *Lactobacilli*. CHX is bacteriostatic for *Mycobaterium*. CHX is also active against yeasts including *Candida albicans* and viruses including HIV, HBV, HCV, Influenza- and Herpes virus. A further advantage of CHX is its low toxicity.

Preferred anti-microbial agents include: Hexitidin, Cetypyridiniumcloride (CPC), Chlorhexidin (CHX), Triclosan, stannous chloride, benzalkonium chloride, non-ionic or ionic surfactants (e.g. quarternary ammonium compounds), alcohols [monomeric, polymeric, mono-alcohols, poly-alcohols (e. g. Xylitol, Sorbitol), aromatic (e. g. phenol)], antimicrobial peptides (e. g. histatins), bactericins (e. g. nisin), antibiotics (e. g. tetracycline), aldehydes (e. g. glutaraldehyde) inorganic and organic acids (e. g. bencoic acid, salicylic acid, fatty acids) or there salts, derivative of such acids such as esters (e. g. p-hydroxy benzoate or other parabenes, lauricidin), enzymes (e. g. lysozyme, oxidases), proteins (e. g. enamel matrix protein, prolin rich proteins), fluoride, EDTA, essential oils (e. g. thymol). Several silver containing components are reported to have an antimicrobial effect, too.

In another embodiment, the dental composition can comprise one or more buffer(s) as an additive, in addition to the water-soluble particles which might already behave like a buffer (e.g. glycine or sodium hydrogen phosphate).

There is no need for a buffer to be present however, if it is present, it is typically present in an amount of at most about 20 wt.-% or of at most about 10 wt.-% or of at most about 5 wt.-% with respect to the amount of the whole composition. Typical ranges include from 0.1 wt.-% to about 20 wt.-% or from 1 wt.-% to about 10 wt.-% with respect to the amount of the whole composition.

Examples of buffers, which can be used, include acetic acid/acetate, tris(hydroxymethyl)aminomethane (TRIS), N-(2-acetamido)-2-aminoethane sulphonic acid (ACES), N-(2-acetamido)imminodiacetate (ADA), N,N-bis(2-hydroxyethyl)-2-aminoethane sulphonic acid (BES), N,N-bis(2-hydroxyethyl)glycine (BICINE), 2,2-bis-(hydroxyethyl)-iminotris(hydroxylmethyl)methane (BIS-TRIS), 2-(cyclohexylamino)ethane sulphonic acid (CHES), 2-[4-(2-hydroxyethyl-1-piperazine)]ethane sulphonic acid (HEPES), 3-[4-(2-hydroxyethyl-1-piperazinyl)]propane sulphonic acid (HEPPS), 2-morpholinoethane sulphonic acid (MES), 3-morpholinopropane sulphonic acid (MOPS), piperazine-1, 4-bis(2-ethane sulphonic acid (PIPES), N-[tris(hydroxymethyl)-methyl]-2-aminoethane sulphonic acid (TES), N-[tris(hydroxymethyl)-methyl]-glycine (TRICINE).

In a further embodiment, the dental composition comprises one or more surfactant(s) as an additive.

There is no need for a surfactant to be present at all. However, if it is present, it is typically present in an amount of at most about 10 wt.-% or of at most about 5 wt.-% or of at most about 2.5 wt.-% with respect to the amount of the whole composition. Typical ranges include from 0.01 wt.-% to about 10 wt.-% or from 2 wt.-% to about 5 wt.-% with respect to the amount of the whole composition.

Examples of surfactant(s) which can be used include water-soluble salts of alkyl sulfates and alkyl ether sulfates having from 10 to 18 carbon atoms in the alkyl moiety, water-soluble salts of sulphonated monoglycerides of fatty acids having from 10 to 18 carbon atoms in the alkyl radical and mixtures thereof. More specific examples include sodium lauryl sulphate and sodium coconut monoglyceride sulphonates.

According to a certain embodiment, the inventive composition comprises
  a water-miscible liquid in an amount of about 90 to about 5 or about 50 to about 10 or about 30 to about 15 wt.-%,
  water-soluble particles in an amount of about 95 to about 10 or about 90 to about 20 or about 80 to about 50 wt.-%, and
  additives in an amount of about 0 to about 30 or about 0 to about 15 or about 0 to about 10 wt.-%,
wt.-% with respect to the whole composition.

One possibility of producing the composition described in the text of the invention is combining, blending or mixing the respective components of the composition.

In particular, the water-soluble particles are combined with the water-miscible liquid and with the additive(s), if present. Combining includes mixing. Mixing can be accomplished by hand or by using a mixing machine such as a speed mixer and/or a kneader.

If desired, the components to be mixed can be milled first until an appropriate particle size is reached. Milling can be accomplished in a ball mill A further aspect of the invention is directed to a kit of parts comprising part I and part II, part I comprising a water-miscible liquid and part II comprising water-soluble particles, part I and part II being essentially free of water and part I and part II being separated from each other before use and wherein the optional additive(s) can be present either in part I or part II or in part I and part II.

Thus, the composition can be provided as a kit of parts, wherein the individual parts contain the components of the composition. The final composition can be obtained by combining (e.g. mixing) the individual parts.

Yet another aspect of the invention is directed to a method of using the composition or the kit of parts described in the text of the invention as dental composition, cleaning agent, polishing agent, or peeling agent (e.g. for skin, hard dental tissue, surfaces of dental filling materials, tongue surfaces and/or orthodontic appliances).

A further aspect of the invention is directed to a kit of parts comprising part A and part B, part A comprising the composition or the kit of parts described in the text of the invention and part B comprising a polishing device.

Polishing devices, which can be used, include devices having a rough surface. The device can have the shape of a cup, brush, disc, or flexible sheet. Examples of dental prophylaxis cups are given in U.S. Pat. No. 5,360,339 (Rosenberg) or U.S. Pat. No. 6,146,140 (Bailey) the disclosures of which are herewith incorporated by reference and regarded as part of the description of the invention. Some of these devices (e.g. polishing discs) are also commercially available and sold under the trade names Prophy Angle™ (3M ESPE Comp.).

The kit may further comprise accessories including applications or dispensing devices such as a syringe, a spoon or a spatula.

The composition described in the text of the invention is preferably provided to the practitioner under hygienic conditions. One possibility to achieve this is storing the composition in a sealed container.

Thus, the composition can typically be packaged into sealable bottles, tubes, vessels or foil bags (including glass or plastic bottles, e.g. equipped with a screw cap). Also specific packaging devices can be used including the holder for a tooth treatment material described in U.S. Pat. No. 5,996,864 (Birglechner).

The composition and appropriate accessories can be packaged and sold together in a so-called introduction kit. Such accessories can include polishing devices as described above, if desired of different sizes.

A further embodiment of the invention is directed to a method of treating a surface comprising the steps of
  applying the composition of the invention on the surface to be treated,
  treating (e.g. polishing) the surface onto which the composition has been applied, typically using a polishing device, preferably a rotating polishing device, and
  optionally removing the remaining composition from the treated surface, e.g. using water.

The term "optionally" indicates that this process step is not necessary, but can be applied, if desired. All steps can be repeated, if desired.

The sequence of the application steps is equal and independent from each other and can also be repeated, if needed. If desired, the composition can be applied with the aid of the polishing device or with the aid of a separate device.

A single polishing step typically lasts for at least about 5 s (seconds) or at least about 20 s (seconds) or at least about 1 min per tooth. Typically, the polishing procedure of a surface of a tooth or a filling material to be treated can be accomplished within about 5 s or within about 1 min.

Surfaces which can be treated include the surface of dental materials (e.g. dental filling materials, dental restorations like inlays, onlays, veneers, dental crowns, and dental bridges), the surface of mammal hard tooth substance (e.g. dental enamel and dentin), mammal skin, wood (e.g. furniture) and metal (e.g. automotive parts).

Typically, the inventive composition does not contain components which are damaging to the surface to be treated.

In this respect, certain embodiments of the dental composition are essentially free of abrasive particles (e.g. less than about 2 or less than about 1 or less than about 0.1 wt.-%) or do not contain abrasive particles at all. Common to most of these substance is typically a comparable high hardness, e.g. above about Mohs 4 or above about 5.

Abrasive particles which are typically used in dentifrices and which might be regarded as damaging include perlite, silica such as sand or quartz, ground glass, silicon carbide, alumina, ilmenite ($FeTiO_3$), zircon oxide, zircon silicate, topaz, $TiO_2$, precipitated lime, chalk, flour of pumice, zeolites, talcum, kaolin, kieselguhr, aluminium oxide, and silicates.

According to a further embodiment the inventive composition typically contains less than about 10 wt.-% or less than about 5 wt.-% of sodium bicarbonate and/or sodium chloride, wt-% with respect to the whole composition.

FIG. 1 shows a SEM (scanning electron microscope) picture of an embodiment of the inventive composition (Example 8) before use as a polishing paste. The picture was obtained with a secondary electron detector at 1.0 kV and $<10^{-4}$ mbar. The glycine particles contained in the inventive composition have rough edges and many small particles are present.

FIG. 2 shows a SEM picture of an embodiment of the inventive composition (Example 8) after use as a polishing paste. The picture was obtained with a secondary electron detector at 1.0 kV and $<10^{-4}$ mbar. What can be seen is that the individual glycine particles contained in the inventive composition do not have rough edges anymore, but show a comparable rounded shape. Many of the small particles dissolved during the treatment.

The following examples are given to illustrate, but not limit, the scope of this invention. Unless otherwise indicated, all parts and percentages are by weight and all tests were conducted at ambient conditions (23° C.; 50% humidity and room pressure).

Examples

Measurements

A Consistency

The consistency was evaluated in accordance with ISO 4823:2000:

Slightly overfill the dispensing tube (capable of a volume of 0.5+/−0.02 ml) with composition and strike off excess material to form the increment.

Push the increment-extruding end of the plunger to expel the test increment onto the centre of the glass base plate, covered with an approximately 70×70 mm polyethylene sheet.

Centre the glass base plate with the increment on the base of the test instrument under the elevated loading-shaft foot and cover the increment with a second polyethylene sheet (70×70 mm).

Centre the increment on the base of the test instrument directly under the elevated loading-shaft foot.

Place and hold the glass loading plate centred and in contact with the shaft foot.

Allow the 14.7 N load to descend slowly onto the increment.

Allow the total load to rest on the specimen-forming assembly for 5 s.

Lift the foot of the loading shaft from contact with the loading plate and remove the loading plate as well.

Leave the specimen between the polyethylene sheets for making two diametral measurements of the specimen, one across the major diameter of the disc and one across the minor diameter. Calculate the average of the two measurements as the diameter to be considered.

B Water-Solubility

The water-solubility was determined as follows:

800 mg of the composition to be analysed and 8.0 g demineralised water were placed into a 15 ml centrifuge test tube of known weight. The test tube was closed and shaken for 5 minutes to get a smooth slurry. The mixture was centrifuged with centrifugal acceleration of ac=9870 m/s² (=1000-fold gravitational acceleration) for 20 min. The supernatant liquid was decanted.

The next step was done twice: The precipitate was re-suspended with 6 g demineralised water, shaken for 5 min, centrifuged as described above, and the supernatant liquid decanted again.

The remaining (wet) precipitate was kept for 12 h at ambient conditions (23° C.), followed by 12 h drying at 105° C. (+/−3.5° C.). After cooling to room temperature in a desiccator the samples dry weight was determined and used to calculate the water soluble fraction.

Figure 3:
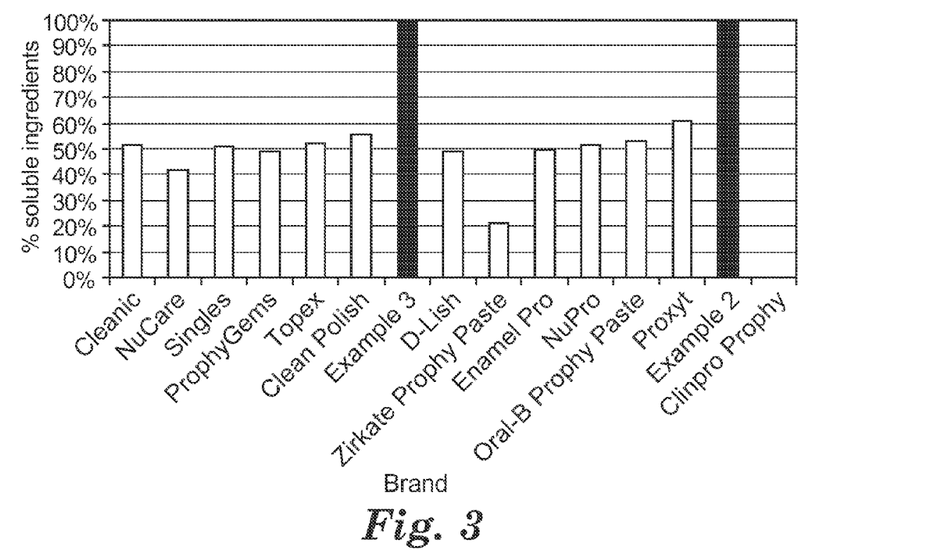
FIG. 3 shows the water-solubility of commercially available polishing pastes vs. an inventive composition.

FIG. 3 shows a diagram comparing the water solubility of various compositions evaluated according to the procedure outlined above.

C Gloss

The gloss was determined using a micro-TRI-gloss reflectometer from BYK Gardner. Per definition it is the reflectometer value (R') which is related to a black glass standard with defined index of refraction (1.567) which equals 100 units.

Before use, the reflectometer was calibrated against the black glass standard. From each specimen 3 reflection values with a geometry (reflection angle) of 60° were determined, and their mean value was calculated.

Preparation of the Specimens:

A sample of the composite material Filtek™ Z250 shade A2 (3M ESPE Comp.) was placed between two (microscopic) glass slides and hardened with dental curing light (Elipar™ Freelight, 3M ESPE) for 20 s according to the instruction for use given by the manufacturer. After curing the glass slides were removed. The gloss value of the sample disc was measured before and after treatment with the pastes tested. The treatment was done using the polishing device Pro-Cup™ (Kerr Comp.; USA) at 1000 rotations per minute for 3 minutes.

Figure 4:
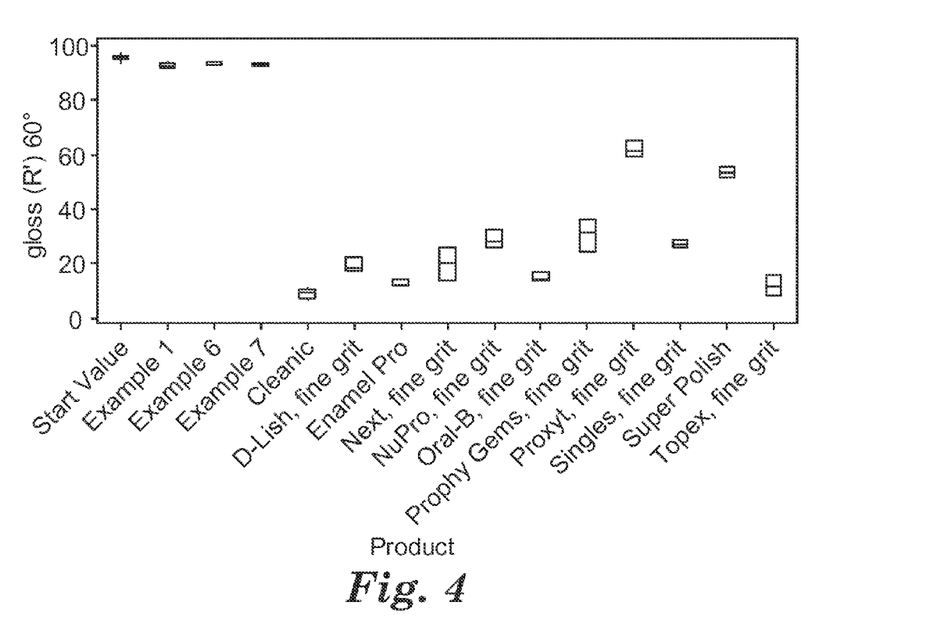
FIG. 4 shows the gloss measured using commercially available polishing pastes vs. an inventive composition.

FIG. 4 shows a boxplot of the measurement of the gloss of various compositions evaluated according to the procedure outlined above.

D Loss of Dentin

Preparation of Specimens

Cut extracted, sound human tooth (not older than 4 weeks since extraction; stored in 0.9% saline solution at 2-8° C.) into 1 mm thick specimen discs (in transversal direction). Dentin specimens must not contain any dental pulp but may be bound by enamel.

Store specimens in demineralised water. The specimens should be stored for the same time and same temperature.
Determine Weight of Specimens
Dry specimens with paper towel.
Weight specimens on a balance.
Polishing Treatment
Mount specimens with double sided sticky tape on a sample holder (e.g. mixing pad)
Repeat the following steps three times:
Apply 5 µl of demineralised water on specimen.
Fill a Pro-Cup™ (Kerr Comp.; USA) with paste (for 2nd and 3rd polishing treatment the same cup was used, refilled with paste, without a cleaning step in between).
Polish in the centre of the specimen for 60 s with 3000 rpm with a dental hand piece; load approximately between 180 and 280 g.
Wipe off used prophylaxis paste on the specimen with a paper towel.
Remove specimens from sample holder.
Rinse off paste with water thoroughly.
Determine Weight of Specimens
Dry specimens with paper towel.
Weight the specimens on a balance.
Loss of dentin=m[mg] (before treatment)−m[mg] (after treatment)

Figure 5:
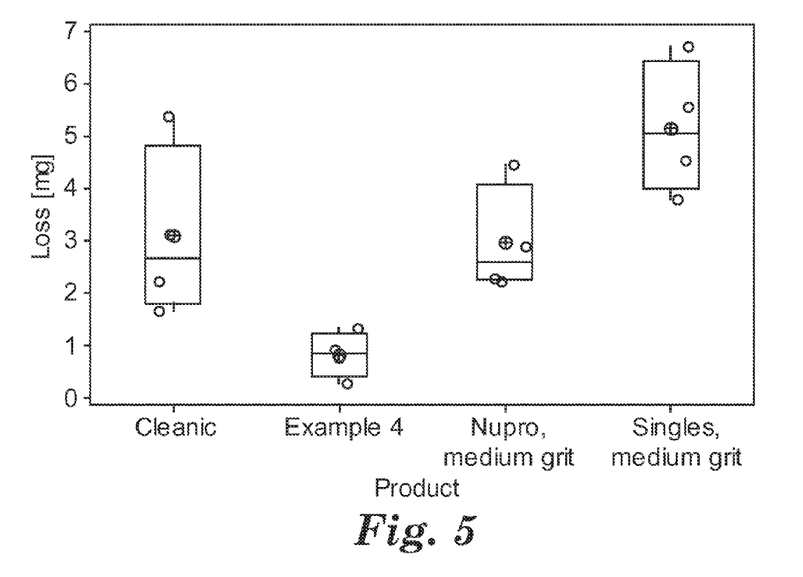
FIG. 5 shows the loss of dentin measured using commercially available polishing pastes vs. an inventive composition.

FIG. 5 shows a boxplot of the measurement of the loss of dentin of various compositions evaluated according to the procedure outlined above.

E Surface Roughness of Bovine Enamel After Paste Treatment

Preparation of Specimens

A specimen of 4×6 mm size, fully covered with enamel was cut from a bovine tooth. The enamel was polished for 1 min using a 10 µm diamond abrasive paper and 3 min using a 1 µm Diamond polishing suspension (1 µm MetaDiMoncrystalline Diamond Suspension, Bühler Comp.) on al Leco Spectrum System 1000 polishing device at a speed of 350.

Polishing Treatment

Place specimens in a sample holder made of a dental impression material (Express™ Penta™ Putty; 3M ESPE Comp.). Impression material and specimen form an edge free plane surface.
Repeat the following steps three times:
Apply 5 µl of demineralised water on disc.
Fill a Pro-Cup™ (Kerr Comp.; USA) with paste (for 2nd and 3rd polishing treatment the same cup is being used without cleaning in between).
Polish the centre of the specimen for 60 s with 3000 rpm on a dental unit.
Wipe off used paste on the specimen with a paper towel.
Rinse off paste with water thoroughly.

Measuring Surface Roughness of Specimens

On each sample disc the surface roughness profiles of 5-7 lines (length 1.25 mm) were measured using a Perthometer MP4 from Mahr GmbH, Germany in accordance with DIN 4768.

The surface roughness of the specimens before and after treatment with the paste was compared (0 s, 1*60 s, 3*60 s).

Figure 6:
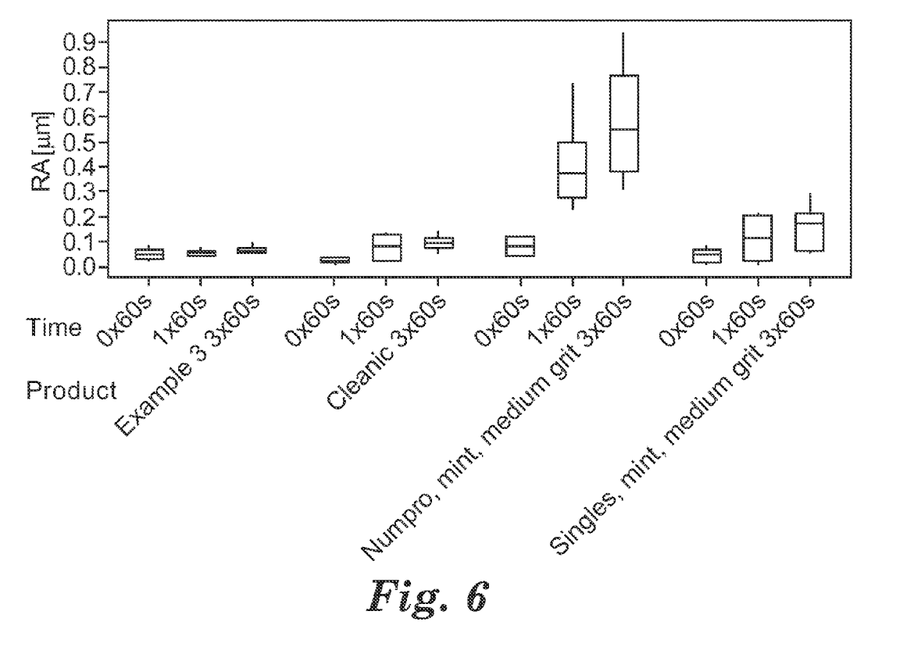
FIG. 6 shows the surface roughness measured using commercially available polishing pastes vs. an inventive composition.

FIG. 6 shows a boxplot of the measurement of the surface roughness of various compositions evaluated according to the procedure outlined above.

F Particle Size

The mean particle size was determined using a commercially available granulometer (Laser Diffraction Particle Size Analysis Instrument, MASERSIZER 2000; Malvern Comp.) according to the instruction of use provided by the manufacturer. When conducting the measurement care has to be taken that the particles are fully dispersed in the dispersing liquid and that the dispersion does not contain air bubbles. The values determined are referred to as volume weighted mean value (µm).

Materials

The following materials were used (Table 1):

TABLE 1

| Name | Description | Availability |
|---|---|---|
| Glycine | Ph. EUR., USP | Sigma-Aldrich |
| Glycerol | Ph. EUR., USP | Merck |
| Carbopol ™ 981 NF | Carboxyvinyl polymer | Lubrizol |
| Sodium fluoride | | Sigma-Aldrich |
| Xylitol | | Sigma-Aldrich |
| Citric acid | | Acros |
| Sodium Polyphosphate | | Sigma-Aldrich |
| Sodium Dihydrogenphosphate | | Merck |
| Stabileze ™ | stabilizer | ISP |
| Cleanic ™ | prophylaxis paste | Kerr |
| NuCare ™, mint, Gentle | prophylaxis paste | Butler |
| Singles ® mint, medium grit | prophylaxis paste | Omni Comp. |
| Singles ® mint, fine grit | prophylaxis paste | Omni Comp. |
| ProphyGems ™ mint, medium grit | prophylaxis paste | Biotrol |
| ProphyGems ™ mint, fine grit | prophylaxis paste | Biotrol |
| Topex ™, medium grit | prophylaxis paste | Sultan |
| Topex ™, fine grit | prophylaxis paste | Sultan |
| Clean Polish ™ | prophylaxis paste | Kerr |
| D-Lish ™ mint, medium grit | prophylaxis paste | Young |
| D-Lish ™ mint, fine grit | prophylaxis paste | Young |
| Zirkate Prophy Paste | prophylaxis paste | DENTSPLY |
| Enamel Pro ™, mint, medium grit | prophylaxis paste | Premier |
| Enamel Pro ™, mint, fine grit | prophylaxis paste | Premier |
| Nupro ™, mint, medium grit | prophylaxis paste | DENTSPLY |
| Nupro ™, mint, fine grit | prophylaxis paste | DENTSPLY |
| Oral-B ™ Prophy Paste, mint, medium grit | prophylaxis paste | Oral-B |
| Oral-B ™ Prophy Paste, mint, fine grit | prophylaxis paste | Oral-B |
| Proxyt ™, medium grit | prophylaxis paste | Ivoclar Vivadent |
| Proxyt ™, fine grit | prophylaxis paste | Ivoclar Vivadent |
| Super Polish | prophylaxis paste | Kerr |
| Next ™, fine grit | Prophylaxis paste | Preventech |

Synthesis of a Composition According to the Invention

The respective components of the inventive composition were used as provided by the manufacturer or ground to an appropriate grain size, if needed, using a ball mill. The ground components were mixed with the water-miscible liquid using a speed mixer and/or a kneader. Compositions Nos. 1 to 6 are inventive, compositions. Nos. 4 to 18 are commercially available materials.

Example Compositions

Example 1

| | |
|---|---|
| Glycine (231 μm) | 74.6 wt-% |
| Glycerol | 22.6 wt-% |
| Carbopol 981 NF | 0.1 wt-% |
| Sodium fluoride | 2.7 wt-% |

Example 2

| | |
|---|---|
| Glycine (176 μm) | 77.3 wt-% |
| Glycerol | 22.6 wt-% |
| Stabileze | 0.05 wt-% |

Example 3

| | |
|---|---|
| Glycine (147 μm) | 77.3 wt-% |
| Glycerol | 22.6 wt-% |
| Carbopol 981 NF | 0.1 wt-% |

Example 4

| | |
|---|---|
| Glycine (131 μm) | 77.3 wt-% |
| Glycerol | 22.7 wt-% |

Example 5

| | |
|---|---|
| Xylitol (266 μm) | 67.5 wt-% |
| Glycerol | 32.5 wt-% |

Example 6

| | |
|---|---|
| Glycine (129 μm) | 77.3 wt-% |
| Glycerol | 22.3 wt-% |
| Stabileze | 0.4 wt-% |

Example 7

| | |
|---|---|
| Glycine (161 μm) | 77.3 wt-% |
| Glycerol | 22.6 wt-% |
| Carbopol 981 NF | 0.08 wt-% |

Example 8

| | |
|---|---|
| Glycine (163 μm) | 77.3 wt-% |
| Glycerol | 22.7 wt-% |

The following compositions were tested: Cleanic™ from KerrHawe Comp, Nupro™ (medium grit, mint flavour) from Dentsply Comp., Singles™ (medium grit, mint flavour) from Omni Comp., Example 1, Example 2, Inventive Example 3, Example 4, Example 6 and Example 7.

The results for water-solubility are shown in FIG. 3.

The results for the measurement of Gloss are shown in FIG. 4

The results for the measurement of Loss of Dentin are shown in Table 2 and FIG. 5

The results for the analysis of Surface Roughness are shown in Table 3 and FIG. 6.

TABLE 2

Test results: Loss of Dentin [mg]:

| Product | N | Mean | StDev |
|---|---|---|---|
| Cleanic | 4 | 3.100 | 1.635 |
| Nupro | 4 | 2.973 | 1.043 |
| Singles | 4 | 5.160 | 1.268 |
| Example 4 | 4 | 0.830 | 0.435 |

(StDev = Standard Deviation)

TABLE 3

Surface Roughness RA [μm]

| Product | N | Mean | StDev |
|---|---|---|---|
| Results for Time = 0 × 60 s (before treatment) | | | |
| Cleanic | 5 | 0.0220 | 0.00837 |
| Nupro | 5 | 0.0800 | 0.0400 |
| Singles | 8 | 0.0425 | 0.02712 |
| Example 3 | 6 | 0.0467 | 0.02160 |
| Results for Time = 1 × 60 s treatment | | | |
| Cleanic | 6 | 0.0750 | 0.0536 |
| Nupro | 6 | 0.4017 | 0.1745 |
| Singles | 6 | 0.1100 | 0.0959 |
| Example 3 | 8 | 0.05250 | 0.01165 |
| Results for Time = 3 × 60 s treatment | | | |
| Cleanic | 7 | 0.0943 | 0.0294 |
| Nupro | 6 | 0.5750 | 0.2277 |
| Singles | 7 | 0.1514 | 0.0928 |
| Example 3 | 6 | 0.06333 | 0.0163 |

The test results are summarized in Table 4.

TABLE 4

| | Components | Roughness (3 × 60 s) | Loss of Dentin | Gloss R' | Water-solubility [wt.-%] |
|---|---|---|---|---|---|
| 1 | Example 1 | n.m. | n.m. | 92.7 ± 0.8 | n.m. |
| 2 | Example 2 | n.m. | n.m. | n.m. | 100% |
| 3 | Example 3 | 0.063 ± 0.016 | n.m. | n.m. | 100% |

TABLE 4-continued

| Components | Roughness (3 × 60 s) | Loss of Dentin | Gloss R' | Water-solubility [wt.-%] |
|---|---|---|---|---|
| 4 Example 4 | n.m. | 0.8 ± 0.4 | n.m. | n.m. |
| 5 Example 5 | n.m. | n.m. | n.m. | n.m. |
| 6 Example 6 | n.m. | n.m. | 93.8 ± 0.5 | n.m. |
| 7 Example 7 | n.m. | n.m. | 93.1 ± 0.5 | n.m. |
| 8 Example 8 | n.m. | n.m. | n.m. | n.m. |
| 9 Cleanic | 0.094 ± 0.029 | 3.1 ± 1.6 | 9.2 ± 1.7 | 52% |
| 10 NuCare; Gentle, mint | n.m. | n.m. | n.m. | 42% |
| 11 Singles mint, medium grit | 0.151 ± 0.093 | 5.1 ± 1.3 | n.m. | 51% |
| 12 Singles, mint, fine grit | n.m. | n.m. | 27.2 ± 1.3 | n.m. |
| 13 ProphyGems mint, medium grit | n.m. | n.m. | n.m. | 49% |
| 14 ProphyGems, mint, fine grit | n.m. | n.m. | 30.7 ± 5.8 | n.m. |
| 15 Topex, medium grit | n.m. | n.m. | n.m. | 52% |
| 16 Topex, fine grit | n.m. | n.m. | 12.0 ± 3.9 | n.m. |
| 17 Clean Polish | n.m. | n.m. | n.m. | 56% |
| 18 D-Lish mint, medium | n.m. | n.m. | n.m. | 49% |
| 19 D-Lish, fine grit | n.m. | n.m. | 19.4 ± 2.4 | n.m. |
| 20 Zirkate Prophy Paste | n.m. | n.m. | n.m. | 21% |
| 21 Enamel Pro, mint, medium | n.m. | n.m. | n.m. | 50% |
| 22 Enamel Pro, mint, fine grit | n.m. | n.m. | 12.9 ± 1.4 | n.m. |
| 23 Nupro, mint, medium grit | 0.575 ± 0.228 | 3.0 ± 1.0 | n.m. | 52% |
| 24 Nupro, mint, fine grit | n.m. | n.m. | 28.7 ± 3.3 | n.m. |
| 25 Oral-B Prophy Paste, mint medium | n.m. | n.m. | n.m. | 53% |
| 26 Oral-B Prophy Paste, mint, fine grit | n.m. | n.m. | 15.0 ± 1.8 | n.m. |
| 27 Proxyt, medium grit | n.m. | n.m. | n.m. | 61% |
| 28 Proxyt, fine grit | n.m. | n.m. | 61.9 ± 2.9 | n.m. |
| 29 Super Polish | n.m. | n.m. | 53.5 ± 2.0 | n.m. |
| 30 Next, fine grit | n.m. | n.m. | 20.0 ± 6.0 | n.m. | n.m. = not measured

The invention claimed is:

1. A water-soluble dental composition comprising
a water miscible liquid selected from the group consisting of polyols, glycerol ether, alcohols and mixtures thereof,
at least 10 wt.-% water-soluble particles, the water-soluble particles comprising substances selected from organic acids and their salts, amino acids and their salts, sugars, and mixtures thereof, and
less than about 5 wt.-% of water-insoluble particles having a Mohs hardness of above about 5,
the water-soluble composition being essentially free of water, wt.-% with respect to the whole composition, and wherein the composition contains less than about 10 wt.-% of either or more of the following components: sodium bicarbonate, sodium carbonate, sodium chloride, magnesium sulfate and starch, wt-% with respect to the whole composition.

2. The composition according to claim 1 being characterized by at least one or more of the following features:
Consistency: less than about 35 mm at 25° C.,
pH-Value: above about 2, if 10 g of the composition are dissolved in 30 g water,
the composition containing less than about 5 wt.-% water.

3. The composition according to claim 1, wherein the water-soluble particles are characterized by at least one or more of the following features:
Mean particle size: below about 500 μm,
Density: below about 4.5 g/ml,
Molecular weight of the substance the particles are comprised of: below about 10,000 g/mol.

4. The composition according to claim 1, wherein the water-miscible liquid is characterized by at least one or more of the following features:
Boiling point: above about 50° C. measured at 1013 mbar,
Viscosity: below about 100 Pa*s measured at 23° C.,
Molecular weight: below about 100,000.

5. The composition according to claim 1 comprising
the water-miscible liquid in an amount of about 90 to about 5 wt.-%,
the water-soluble particles in an amount of about 90 to about 10 wt.-% and
further comprising additives in an amount of about 0 to about 30 wt.-%, wt.-% with respect to the whole composition.

6. The composition according to claim 1 further comprising at least one additive selected from the group consisting of stabilizer(s), fluoride releasing agent(s), anti-microbial agent(s), colourant(s), buffer(s), surfactant(s), phosphate releasing agent(s) and mixtures thereof.

7. A kit of parts comprising part A and part B, part A comprising the water-soluble dental composition according to claim 1 and part B comprising a polishing device.

8. The composition according to claim 1, wherein the water-soluble particles comprise at least one of citric acid, ascorbic acid, ketoglutaric acid, pyruvic acid, sodium lactate, glycine, alanine, glutamine, glutamic acid, serine, valine, leucine, iso-leucine, potassium glutamate, sodium glutamine, xylitol, sorbitol, glucose, fructose, saccharose, and a combination thereof.

9. The water-soluble dental composition of claim 1, comprising
less than about 2 wt.-% of starch.

10. The water-soluble dental composition of claim 1, wherein the composition contains less than about 1 wt.-% of water-insoluble particles.

11. The water-soluble dental composition of claim 1, wherein the composition contains less than about 2 wt.-% of water-insoluble particles.

12. The water-soluble dental composition of claim 1, wherein the composition contains less than about 0.1 wt.-% of water-insoluble particles.

13. The water-soluble dental composition of claim 1, wherein the composition is essentially free of water-insoluble particles.

14. The water-soluble dental composition of claim 1, wherein the water-insoluble particles are abrasive particles selected from the group consisting of perlite, silica, ground glass, silicon carbide, alumina, ilmenite, zircon oxide, zircon silicate, topaz, titanium dioxide, precipitated lime, chalk, flour of pumice, zeolites, talcum, kaolin, kieselguhr, aluminium oxide, and silicates.

* * * * *

UNITED STATES PATENT AND TRADEMARK OFFICE
CERTIFICATE OF CORRECTION

PATENT NO. : 8,858,921 B2
APPLICATION NO. : 12/921840
DATED : October 14, 2014
INVENTOR(S) : Brenda Schmid It is certified that error appears in the above-identified patent and that said Letters Patent is hereby corrected as shown below:

Title Page, Column 2 References Cited (Other Publications)
Line 2, Delete "Dentrifrice" and insert -- Dentifrice --, therefor.

In the Specification
Column 2
Line 18, Delete "appliances)," and insert -- appliances). --, therefor.

Column 7
Line 29, Delete "glycerole" and insert -- glycerol --, therefor.
Line 30, Delete "buthyl" and insert -- butyl --, therefor.

Column 8
Line 30, Delete "polysaccaride" and insert -- polysaccharide --, therefor.
Line 34, Delete "polysaccaride" and insert -- polysaccharide --, therefor.
Line 35, Delete "monosaccaride" and insert -- monosaccharide --, therefor.

Column 9
Line 34-35, Delete "coplymere" and insert -- copolymere --, therefor.
Line 54, Delete "thereof" and insert -- thereof. --, therefor.

Column 10
Line 5, Delete "Neazopon" and insert -- Neozapon --, therefor.
Line 21, Delete "trimetaphopshate," and insert -- trimetaphosphate, --, therefor.
Line 35-36, Delete "glutaraldyde, phtalaldehyde" and insert -- glutaraldehyde, phthalaldehyde --, therefor.
Line 44, Delete "Chlorohexidine" and insert -- Chlorhexidine --, therefor.
Line 45, Delete "diacatate" and insert -- diacetate --, therefor.
Line 51, Delete "Mycobaterium." and insert -- Mycobacterium. --, therefor.

Signed and Sealed this
Thirty-first Day of March, 2015

Michelle K. Lee
*Director of the United States Patent and Trademark Office*

Column 10
Line 55-56, Delete "Hexitidin, Cetypyridiniumcloride" and insert -- Hexetidine, Cetylpyridiniumchloride --, therefor.
Line 58, Delete "quarternary" and insert -- quaternary --, therefor.
Line 61, Delete "bactericins" and insert -- bacteriocins --, therefor.
Line 63, Delete "bencoic" and insert -- benzoic --, therefor.
Line 65, Delete "parabenes," and insert -- parabens, --, therefor.
Line 67, Delete "prolin" and insert -- proline --, therefor.

Column 11
Line 67, Delete "mill" and insert -- mill. --, therefor.

Column 15
Line 36, Delete "MetaDiMoncrystalline" and insert -- MetaDiMonocrystalline --, therefor.

Column 16
Line 5, Delete "Express™" and insert -- Express™, --, therefor.
Line 28, Delete "MASERSIZER" and insert -- MASTERSIZER --, therefor.

Column 18
Line 20-21, Delete "FIG. 4" and insert -- FIG. 4. --, therefor.
Line 23, Delete "FIG. 5" and insert -- FIG. 5. --, therefor.